United States Patent
Huang et al.

(10) Patent No.: US 9,619,876 B2
(45) Date of Patent: Apr. 11, 2017

(54) DETECTING DEFECTS ON WAFERS BASED ON 2D SCATTER PLOTS OF VALUES DETERMINED FOR OUTPUT GENERATED USING DIFFERENT OPTICS MODES

(71) Applicant: KLA-Tencor Corporation, Milpitas, CA (US)

(72) Inventors: Junqing Huang, Fremont, CA (US); Lisheng Gao, Saratoga, CA (US)

(73) Assignee: KLA-Tencor Corp., Milpitas, CA (US)

(*) Notice: Subject to any disclaimer, the term of this patent is extended or adjusted under 35 U.S.C. 154(b) by 269 days.

(21) Appl. No.: 13/796,955

(22) Filed: Mar. 12, 2013

(65) Prior Publication Data

US 2014/0270474 A1 Sep. 18, 2014

(51) Int. Cl.
*G06K 9/00* (2006.01)
*G06T 7/00* (2017.01)
(Continued)

(52) U.S. Cl.
CPC ........... *G06T 7/0004* (2013.01); *G01N 21/88* (2013.01); *G01N 21/8803* (2013.01); *G01N 21/9501* (2013.01); *G01N 21/956* (2013.01); *G01N 21/95607* (2013.01); *G06T 7/001* (2013.01); *G06T 7/0002* (2013.01); *G01N 2021/8825* (2013.01); *G06T 2207/10061* (2013.01);
(Continued)

(58) Field of Classification Search
CPC ........... G01N 2021/8825; G01N 21/17; G01N 21/88; G01N 21/8803; G01N 21/8806; G01N 21/9501; G01N 21/956; G01N 21/95607; G01N 21/95615; G01N 2021/1734; G01N 2021/1736; G01N 2021/1738; G01N 2021/8809; G01N 2021/8822; G01N 2021/8835; G06T 7/0002; G06T 7/0004; G06T 7/0006; G06T 7/0008; G06T 7/001; G01R 31/308; G01R 31/309; G01R 31/311
USPC .................................. 382/141, 144–150, 152
See application file for complete search history.

(56) References Cited

U.S. PATENT DOCUMENTS

| 5,495,535 A | 2/1996 | Smilansky et al. |
| 6,614,924 B1 | 9/2003 | Aghajan |
| (Continued) | | |

FOREIGN PATENT DOCUMENTS

JP 2007-212201 8/2007

OTHER PUBLICATIONS

International Search Report and Written Opinion for PCT/US2014/023827 mailed Jul. 11, 2014.

*Primary Examiner* — Eric Rush
(74) *Attorney, Agent, or Firm* — Ann Marie Mewherter

(57) ABSTRACT

Methods and systems for detecting defects on a wafer are provided. One method includes determining difference values for pixels in first output for a wafer generated using a first optics mode of an inspection system and determining other values for pixels in second output for the wafer generated using a second optics mode of the inspection system. The first and second optics modes are different from each other. The method also includes generating a two-dimensional scatter plot of the difference values and the other values for the pixels in the first and second output corresponding to substantially the same locations on the wafer. The method further includes detecting defects on the wafer based on the two-dimensional scatter plot.

27 Claims, 1 Drawing Sheet

(51) Int. Cl.
*G01N 21/95* (2006.01)
*G01N 21/956* (2006.01)
*G01N 21/88* (2006.01)

(52) U.S. Cl.
CPC ............ *G06T 2207/20076* (2013.01); *G06T 2207/30148* (2013.01)

(56) References Cited

U.S. PATENT DOCUMENTS

| | | | |
|---|---|---|---|
| 6,912,304 | B1 | 6/2005 | Aghajan |
| 7,113,628 | B1 * | 9/2006 | Obara et al. ................... 382/149 |
| 7,440,607 | B1 | 10/2008 | Lin et al. |
| 8,126,255 | B2 | 2/2012 | Bhaskar et al. |
| 8,223,327 | B2 | 7/2012 | Chen et al. |
| 8,467,047 | B2 | 6/2013 | Chen et al. |
| 8,605,275 | B2 | 12/2013 | Chen et al. |
| 2002/0161534 | A1 | 10/2002 | Adler et al. |
| 2005/0092899 | A1 | 5/2005 | Wolf et al. |
| 2006/0002604 | A1 * | 1/2006 | Sakai et al. ................... 382/141 |
| 2006/0215902 | A1 * | 9/2006 | Shibuya ............... G06K 9/6221 382/149 |
| 2006/0233434 | A1 * | 10/2006 | Hamamatsu ......... G06K 9/2027 382/141 |
| 2007/0177787 | A1 * | 8/2007 | Maeda .................... G06T 7/001 382/141 |
| 2008/0285023 | A1 * | 11/2008 | Tsai et al. ................... 356/237.5 |
| 2008/0297783 | A1 * | 12/2008 | Urano et al. ............... 356/237.5 |
| 2009/0287440 | A1 | 11/2009 | Kulkarni et al. |
| 2010/0188657 | A1 * | 7/2010 | Chen et al. ............... 356/237.5 |
| 2011/0320149 | A1 | 12/2011 | Lee et al. |
| 2012/0002860 | A1 | 1/2012 | Sakai et al. |
| 2012/0141012 | A1 * | 6/2012 | Sakai et al. ................... 382/149 |
| 2012/0296576 | A1 * | 11/2012 | Shibata ............... G01B 11/303 702/40 |
| 2013/0035876 | A1 | 2/2013 | Huang et al. |

\* cited by examiner

DETECTING DEFECTS ON WAFERS BASED ON 2D SCATTER PLOTS OF VALUES DETERMINED FOR OUTPUT GENERATED USING DIFFERENT OPTICS MODES

BACKGROUND OF THE INVENTION

1. Field of the Invention

This invention generally relates to detecting defects on a wafer. Certain embodiments relate to detecting defects on a wafer using a two-dimensional scatter plot generated from output generated by different optics modes of an inspection system.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Some currently available inspection systems are configured to inspect a wafer with more than one detection channel, to detect defects on the wafer by separately processing the data acquired by each of the channels, and to classify the defects by separately processing the data acquired by each of the channels. The defects detected by each of the individual channels may also be further processed separately, for example, by generating different wafer maps, each illustrating the defects detected by only one of the individual channels. The defect detection results generated by more than one channel of such a system may then be combined using, for example, Venn addition of the individual wafer maps. Such previously used inspection methods, therefore, do not leverage the output generated by the inspection system at the pixel level, but rather combine the results at the wafer map level as the final result.

Accordingly, it would be advantageous to develop methods and systems for detecting defects on a wafer that make better use of the inspection system output to provide increased defect detection sensitivity.

SUMMARY OF THE INVENTION

The following description of various embodiments is not to be construed in any way as limiting the subject matter of the appended claims.

One embodiment relates to a computer-implemented method for detecting defects on a wafer. The method includes determining difference values for pixels in first output for a wafer generated using a first optics mode of an inspection system. Determining the difference values includes subtracting a characteristic of each of the pixels in the first output for a reference die on the wafer from the characteristic of its corresponding pixel in the first output for a test die on the wafer. The method also includes determining other values for pixels in second output for the wafer generated using a second optics mode of the inspection system. Determining the other values includes determining a value of another characteristic of each of the pixels in the second output for the reference die and the other characteristic of its corresponding pixel in the second output for the test die. The first and second optics modes are different from each other. The method further includes generating a two-dimensional scatter plot of the difference values and the other values for the pixels in the first and second output corresponding to substantially the same locations in the test die. In addition, the method includes detecting defects in the test die on the wafer based on the two-dimensional scatter plot. Determining the difference values, determining the other values, generating the two-dimensional scatter plot, and detecting the defects are performed by a computer system.

Each of the steps of the method described above may be performed as described further herein. The method described above may include any other step(s) of any other method(s) described herein. The method described above may be performed using any of the systems described herein.

Another embodiment relates to a non-transitory computer-readable medium storing program instructions executable on a computer system for performing a method for detecting defects on a wafer. The method includes the steps of the computer-implemented method described above, which may be performed as described further herein. In addition, the method for which the program instructions are executable may include any other step(s) of any other method(s) described herein. The non-transitory computer-readable medium may be further configured as described herein.

An additional embodiment relates to a system configured to detect defects on a wafer. The system includes an inspection subsystem configured to direct light to a wafer and detect light from the wafer to thereby generate first output for the wafer with a first optics mode and second output for the wafer with a second optics mode. The first and second optics modes are different from each other. The system also includes a computer subsystem configured for determining the difference values, determining the other values, generating the two-dimensional scatter plot, and detecting the defects as described above. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
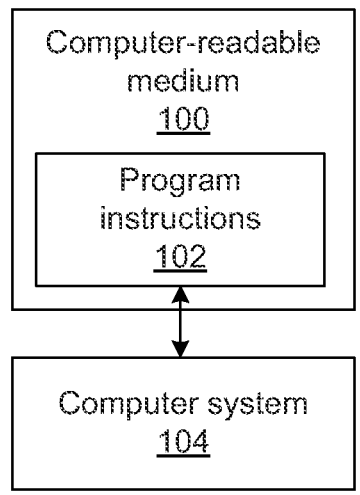
FIG. 1 is a block diagram illustrating one embodiment of a non-transitory computer-readable medium storing program instructions executable on a computer system for performing one or more of the method embodiments described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for detecting defects on a wafer. The method includes determining difference values for pixels in first output for a wafer generated using a first optics mode of an inspection system. The first output may include any suitable output such as image signals or image data and may be generated as described further herein. The first optics mode and the inspection system may be configured as described further herein. Determining the difference values includes subtracting a characteristic of each of the pixels in the first output for a reference die on the wafer from the characteristic of its corresponding pixel in the first output for a test die on the wafer. The characteristic of the pixels that is used for the subtracting may include intensity or gray level intensity or any other suitable characteristic. The test die and the reference die may include any two dies on the wafer such as two dies that are adjacent to each other on the wafer. However, any other reference die known in the art may be used in the embodiments described herein.

The difference values may be values for a difference between pixels in the first output from one die on the wafer to another die on the wafer. Therefore, determining the difference values may be performed in a manner similar to the comparison step of a die-to-die inspection process. However, in one embodiment, the difference values are values for a linearly filtered difference, a match filtered difference, a non-linear filtered difference, a normalized difference, or a square root of a product of two differences. These difference values may be determined in any suitable manner using any suitable method and/or algorithm. The pixels in the first output for which the difference values are determined may include all of the pixels in the first output or only some of the pixels in the first output. For example, if the inspection is to be performed in only a portion of the wafer such as only a logic region of the dies on the wafer, then the difference values may be determined for only the pixels corresponding to the logic region.

The method also includes determining other values for pixels in second output for the wafer generated using a second optics mode of the inspection system. The second output may include any suitable output such as image signals or image data and may be generated as described further herein. The second optics mode may be configured as described further herein. Determining the other values includes determining a value of another characteristic of each of the pixels in the second output for the reference die and the other characteristic of its corresponding pixel in the second output for the test die. The other values may include values for a median between corresponding pixels in the second output. However, in one embodiment, the other values are values for a dilated median or a range of median values between corresponding pixels in the second output. These other values may be determined using any suitable method and/or algorithm. The pixels in the second output for which the other values are determined may correspond to the pixels for which the difference values are determined.

The characteristic of the pixels that is used for determining the other values may include intensity or gray level intensity or any other suitable characteristic. In one embodiment, the characteristic and the other characteristic are intensity of the pixels in the first output and the second output, respectively. Therefore, the characteristics used to determine the difference and other values may be the same characteristic, and the pixels in the first and second output will most likely have different values for that characteristic.

The first and second optics modes are different from each other. An optics mode may be generally defined as a set of values for optical parameters of an inspection system that are used together to generate output for the wafer. The first and second optics modes may be different in imaging modes, polarization states, wavelengths, etc. In addition, the first and second optics modes may be different in only one optical parameter of the inspection system or more than one optical parameter of the inspection system. For example, the first and second optics modes may be different in the detectors used for the modes with the same values for all other optical parameters of the inspection system. Alternatively, the first and second optics modes may be different in the detectors and illumination wavelengths used for the modes with or without the same values for all other optical parameters of the inspection system. Multiple optics modes offer new context of the wafer pattern and structures surrounding defects of interest (DOIs) on the wafer.

In one embodiment, the first and second output are generated in the same pass of an inspection process performed on the wafer by the inspection system. For example, depending on the configuration of the inspection system and the first and second optics modes, the first and second output may be generated simultaneously in the same pass. In one such example, if the first and second modes are defined by different detection polarizations and if the inspection system includes two detectors coupled to two different polarizing components, the first and second output may be detected in the same pass or scan of the wafer. Additional passes may or may not be performed in the same inspection process. Additional output in other optics mode(s) may or may not be generated in the same inspection process during the same scan as that which produces the first and second output or in a different scan.

In another embodiment, the first and second output are generated in different passes of a single inspection process performed on the wafer by the inspection system. For example, depending on the configuration of the inspection system and the first and second optics modes, the first and second output may be generated sequentially in different passes or scans of a multi-pass or multi-scan inspection process. In one such example, if the first and second modes are defined by different detection polarizations and if the inspection system includes only one detector, the first and second output may be generated in different passes or scans of the wafer between which a polarizing component in the path of the detector is changed. Additional passes may or may not be performed in the same inspection process. Additional output may or may not be generated in the same inspection process during one of the scans that produces the first or second output or in a different scan of the same inspection process.

In some embodiments, the first and second output are generated in different passes of different inspection processes performed on the wafer by the inspection system. In such embodiments, the inspection system may be a virtual inspector (VI) such as that described in U.S. Pat. No. 8,126,255 issued on Feb. 28, 2012 to Bhaskar et al., which is incorporated by reference, and the different inspection processes may be performed by one or more other inspection systems such as any one or some combination of the inspection systems described further herein, In this manner, the first and second output may be generated by different inspection systems having completely different optical and/or electron beam configurations.

In some embodiments, the inspection system is configured as a bright field (BF) inspection system, and the first and second output are responsive to light specularly reflected from the wafer. In this manner, the first and second output may be responsive to specularly reflected light detected by the inspection system. The inspection system may also be configured for BF and another mode of inspection such as dark field (DF) inspection. In addition, the inspection system may be configured for inspection of patterned wafers and possibly also unpatterned wafers. Furthermore, the embodiments described herein can be used not only for BF/DF inspection systems, but also with e-beam inspection and/or review systems. Therefore, although certain embodiments and examples are described herein with respect to light-based inspection systems, all embodiments and examples are equally applicable to electron beam-based systems.

The computer-implemented method may include acquiring the first and second output using the inspection system. For example, acquiring the first and second output may include scanning light over the wafer and generating first and second output responsive to light reflected from the wafer detected by the inspection system during the scanning. In this manner, acquiring the first and second output may include scanning the wafer. However, acquiring the first and second output does not necessarily include scanning the wafer. For example, acquiring the first and second output may include acquiring the first and second output from a storage medium in which the first and second output has been stored (e.g., by the inspection system). Acquiring the first and second output from the storage medium may be performed in any suitable manner, and the storage medium from which the output is acquired may include any of the storage media described herein.

The method also includes generating a two-dimensional (2D) scatter plot of the difference values and the other values for the pixels in the first and second output corresponding to substantially the same locations in the test die. For example, the other values (e.g., some type of median values) for the pixels in the second output may be plotted along the y-axis, and the difference values for the pixels in the first output may be plotted along the x-axis. The 2D scatter plot may be generated using any suitable method and/or algorithm. The pixels in the first and second output corresponding to substantially the same locations in the test die may be identified in any suitable manner (e.g., based on die-relative positions corresponding to the pixels in the first and second output).

In some embodiments, the other values are values for a median, a dilated median, or a range of median values. These values can be determined in any suitable manner. The scatter plot analysis may be extended by using the dilated median instead of the median in the-y axis of the scatter plot. The median frame can be quieter and can misrepresent pixels near wafer patterns. Utilizing dilated median may better arbitrate pixels surrounded with different patterns. Although a variety of other values may be used in the y-axis or the segmentation axis of the scatter plot, median, dilated median, and range of median are ways of segmentation (or arbitration) of pixels that provide better separation between DOI and nuisance.

The method further includes detecting defects in the test die on the wafer based on the 2D scatter plot. Defect detection may therefore be performed based on information generated by different optics states used to generate the 2D scatter plot. The embodiments described herein therefore combine information from multiple modes at the 2D scatter plot level to better separate DOIs from nuisance. For example, the embodiments described herein better leverage the fact that different optics states provide different perspectives of the pattern surrounding defects thereby offering the potential to better separate DOIs from real events that the user does not care about (nuisances). In addition, the embodiments described herein take advantage of the real signal from DOIs at one optics mode or pass (difference values) and also exploit the coincidence of the event locations from another optics mode or pass that may have no signal for DOIs but can differentiate previous layer defects (e.g., the scanning electron microscope (SEM) non-visuals (SNVs)) and nuisances better. Furthermore, the scatter plots described herein may have better noise distribution for DOIs and thus provide better detection. In this manner, by combining information at the 2D scatter plot level, one can leverage both differentiation and pattern structure information among different optics modes (or different inspection passes). This allows one to differentiate DOIs with weak signal and suppress nuisance events by exploiting their respective presentations in the 2D scatter plot from different optics modes. As such, the embodiments described herein can be used to enhance the sensitivity of wafer inspection systems. In addition, the embodiments described herein can improve DOI sensitivity and reduce nuisance in detection.

In one embodiment, detecting the defects includes identifying outliers in the 2D scatter plot and determining if the outliers correspond to defects. For example, by combining information from multiple optics states at the outlier detection (2D scatter plot) stage, one has the ability to arbitrate real events that are previous layer events (e.g., SNVs) or other distortions (e.g., distortions that are not yield preventing). Therefore, the embodiments described herein provide opportunities for enhancement of separation between DOIs and nuisances through outlier detection. Determining if the outliers correspond to defects may be performed in any suitable manner. In some embodiments, determining if the outliers correspond to defects or DOIs may include some kind of filtering based on one or more characteristics of the identified outliers.

In another embodiment, detecting the defects includes separating the 2D scatter plot into two or more segments and separately performing defect detection in each of the two or more segments. For example, by combining information from multiple optics states at the outlier detection (2D scatter plot) stage, one has the ability to arbitrate real events that are previous layer events (e.g., SNV) or other distortions (e.g., distortions that are not yield preventing) to different segments of the 2D scatter plot and thus suppress the SNVs and other nuisances.

"Segments" can be generally defined as different portions of an entire range of possible values for the pixels. For instance, in the multiple die auto-thresholding (MDAT) algorithm, which is used by some wafer inspection systems commercially available from KLA-Tencor, Milpitas, Calif., the value for the characteristic of the pixels that is used to define the segments may include median intensity value. In one such illustrative and non-limiting example, if the entire range of median intensity values is from 0 to 255, a first segment may include median intensity values from 0 to 100 and a second segment may include median intensity values from 101 to 255. In this manner, the first segment corresponds to darker areas in the output, and the second segment corresponds to brighter areas in the output. In the embodiments described herein, the segments may be defined along the y axis of the scatter plot. For example, different segments may correspond to different ranges of the median or dilated median values. Such segmentation groups the pixels with similar pattern variation together.

In one embodiment, one or more first defect detection parameters used for the defect detection in a first of the two or more segments are different than one or more second defect detection parameters used for the defect detection in a second of the two or more segments. The defect detection parameters used for different segments may be different in the defect detection algorithms that are assigned to the different segments. Alternatively, the defect detection parameters used for different segments may be different in one or more parameters of the same defect detection algorithm. For example, in some embodiments, the one or more first and second defect detection parameters include different thresholds that are applied to the difference values for the pixels in the first output for the test die. Therefore, different portions of the 2D scatter plot corresponding to the different segments may be inspected with different sensitivities. The defect detection algorithms that are assigned to the different segments or one or more parameters of which are assigned to the different segments may include any suitable defect detection algorithms. For example, the defect detection algorithm may be a segmented auto-thresholding (SAT) algorithm or an MDAT algorithm. Such defect detection algorithms may be particularly suitable for BF inspection.

The embodiments described herein can be referred to as generalized defect detection methods or generalized outlier substrate inspection methods (e.g., generalized MDAT) since the methods can include generating one or more 2D scatter plots for the test die with a variety of different values on the x- and y-axes determined based on a variety of different output for the wafer (e.g., only the first output, only the second output, some combination of different output) generated by one or more passes of the wafer (e.g., generalized MDAT across multiple passes or within a single pass). For example, in one embodiment, the method includes determining other values for the pixels in the first output and generating an additional 2D scatter plot of the difference values and the other values for the pixels in the first output. Such other values and the additional 2D scatter plot may be determined and configured as described further herein.

In some embodiments, the method includes displaying to a user the 2D scatter plot and the additional 2D scatter plot. For example, showing the user the generalized scatter plot generated as described herein allows the user to visualize the difference between an one optics mode (or one pass) scatter plot and the generalized scatter plot. Displaying the 2D scatter plot to the user may be performed in any suitable manner using any suitable display device.

In another embodiment, the method includes performing the detecting step using the 2D scatter plot or the additional 2D scatter plot based on input received from a user. For example, one or more of the scatter plots may be used for defect detection, and the plot or plots that are used for the defect detection may be selected by the user (e.g., after viewing the scatter plots displayed as described above). If more than one scatter plot is used for defect detection, defects detected using each of the different scatter plots may be combined into a single defect population for additional analysis. In addition, the defects detected using more than one scatter plot may be categorized or binned based on the scatter plot or plots in which the defects were detected.

In one embodiment, the method includes displaying to a user the 2D scatter plot and allowing the user to change the difference values and the other values in the 2D scatter plot by selecting the first and second optics modes from multiple optics modes of the inspection system used to generate output for the wafer, selecting the difference values from among different types of difference values that can be determined by the method, and selecting the other values from among different types of other values that can be determined by the method. For example, the method may include showing the user the generalized scatter plot generated as described herein and letting the user choose from among different options for the axes of the scatter plot.

If the 2D scatter plot shape does not change from a single mode scatter plot to the combined mode scatter plot described herein, the method may include detecting DOIs along with nuisances with a relatively low threshold from a first optics mode, then extracting extra information from a second optics mode at the locations of the events detected using the first optics mode, which may be used as additional attributes to filter out the nuisances.

Determining the difference values, determining the other values, generating the 2D scatter plot, and detecting the defects are performed by a computer system, which may be configured as described further herein.

The embodiments described herein have, therefore, a number of advantages over other currently used defect detection methods. For example, some currently used methods perform outlier substrate inspection with one scan, pass, or optics mode. Examples of such methods are described in U.S. Pat. No. 7,440,607 issued Oct. 21, 2008 to Lin et al., which is incorporated by reference as if fully set forth herein. Other currently used methods combine different modes after detection from one mode or through pixel level correlation of modes. Pixel level correlation of modes is described in U.S. Patent Application Publication No. 2010/0188657 published Jul. 29, 2010 by Chen et al., which is incorporated by reference as if fully set forth herein. Unlike the methods described herein, the currently used defect detection methods described above do not take advantage of the fact that different modes can arbitrate to different structures on the wafer and therefore can provide better outlier detection if using first mode difference values in one axis of the scatter plot and second mode other values in the other axis of the scatter plot.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Another embodiment relates to a non-transitory computer-readable medium storing program instructions executable on a computer system for performing a method (i.e., a computer-implemented method) for detecting defects on a wafer. One such embodiment is shown in FIG. 1. For example, as shown in FIG. 1, non-transitory computer-readable medium 100 includes program instructions 102 executable on computer system 104 for performing the method for detecting defects on a wafer described above. The computer-implemented method for which the program instructions are executable may include any other step(s) of any other method(s) described herein.

Program instructions 102 implementing methods such as those described herein may be stored on non-transitory computer-readable medium 100. The computer-readable medium may be a storage medium such as a magnetic or optical disk, a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 104 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 2:
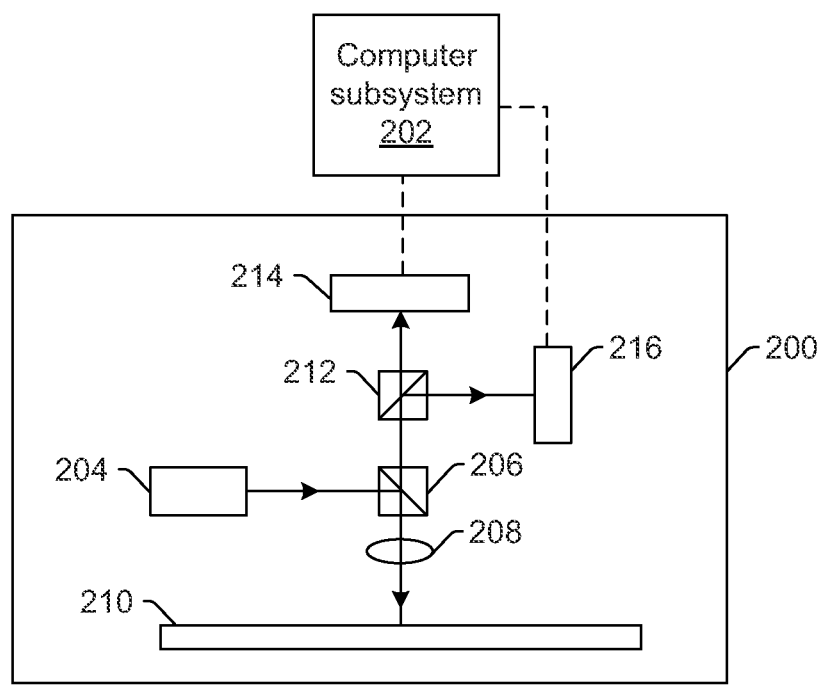
FIG. 2 is a schematic diagram illustrating a side view of one embodiment of a system configured to detect defects on a wafer.

An additional embodiment relates to a system configured to detect defects on a wafer. One embodiment of such a system is shown in FIG. 2. As shown in FIG. 2, the system includes inspection subsystem 200 and computer subsystem 202. The inspection subsystem is configured to direct light to a wafer and detect light from the wafer to thereby generate first output for the wafer with a first optics mode and second output for the wafer with a second optics mode. The first and second optics modes are different from each other. For example, as shown in FIG. 2, the inspection subsystem includes light source 204, which may include any suitable light source known in the art.

Light from the light source may be directed to beam splitter 206, which may be configured to direct the light from the light source though lens 208 to wafer 210. The light source may be coupled to any other suitable elements (not shown) such as one or more condensing lenses, collimating lenses, relay lenses, objective lenses, apertures, spectral filters, polarizing components and the like. As shown in FIG. 2, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light reflected from wafer 210 may be collected and detected by multiple channels of the inspection subsystem during scanning. For example, light specularly reflected from wafer 210 may be collected by lens 208. Lens 208 may include a refractive optical element as shown in FIG. 2. In addition, lens 208 may include one or more refractive optical elements and/or one or more reflective optical elements. Light collected by lens 208 may be directed through beam splitter 206 to beam splitter 212, which may be configured to separate the light into two different paths, one of which is directed to detector 214 and another of which is directed to detector 216. The beam splitters shown in FIG. 2 may include any suitable beam splitters known in the art. The detectors shown in FIG. 2 may include any suitable detectors known in the art such as charge coupled devices (CCDs) or another type of imaging detectors. Detectors 214 and 216 are configured to generate output that is responsive to the specularly reflected light. Therefore, each of the detectors form one channel of the inspection subsystem.

Since the inspection subsystem shown in FIG. 2 is configured to detect light specularly reflected from the wafer, the inspection subsystem is configured as a BF inspection system. Such an inspection subsystem may, however, also be configured for other types of wafer inspection. For example, the inspection subsystem shown in FIG. 2 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for DF inspection. In addition, the inspection subsystem shown in FIG. 2 may be replaced with an e-beam inspection subsystem.

When generating output using multiple optics modes, the values of any optical parameter(s) of the inspection subsystem may be altered in any suitable manner if necessary. For example, to change the illumination polarization states for different optics modes, a polarizing component positioned in the path of the light from the light source may be removed and/or replaced with a different polarizing component. In another example, to change illumination angles for different optics modes, the position of the light source and/or any other optical components used to direct the light to the wafer may be altered in any suitable manner.

In some instances, depending on the selection of the optics modes for use in the embodiments described herein and the configuration of the inspection system, the first and second output may be simultaneously generated using the first and second optics modes, respectively. For instance, in the embodiment shown in FIG. 2, the two detectors may be configured to detect light having different characteristic(s) such as wavelength or polarization and the two detectors may be used to generate the first and second output simultaneously in the same pass of an inspection process (i.e., during a single scan of the wafer). However, the first and second output may be generated in different scans or passes of a single inspection process. For example, the first output may be generated using the first optics mode in one pass or scan of the wafer, an optical parameter of the inspection system may be altered as described above, and then the second output may be generated using the second optics mode in a second pass or scan of the wafer. Furthermore, the inspection systems described herein may be configured to generate two or more output using two or more optics modes of the inspection system. Therefore, the first and second optics modes used in the embodiments described herein may be selected from more than two or all of the available optics modes of the inspection system.

Computer subsystem 202 is configured to acquire the first and second output generated by the inspection subsystem. For example, first and second output generated by the detector(s) during scanning may be provided to computer subsystem 202. In particular, the computer subsystem may be coupled to each of the detectors (e.g., by one or more transmission media shown by the dashed lines in FIG. 2, which may include any suitable transmission media known in the art) such that the computer subsystem may receive the first and second output generated by the detector(s).

The computer subsystem is configured for determining the difference values, determining the other values, generating the 2D scatter plot, and detecting the defects, all of which may be performed as described further herein. The computer subsystem may be configured to perform any other step(s) of any method embodiment(s) described herein. The computer subsystem, the inspection subsystem, and the system may be further configured as described herein.

It is noted that FIG. 2 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the 29xx/28xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
   determining difference values for pixels in first output for a wafer generated using a first optics mode of an inspection system, wherein said determining comprises subtracting a characteristic of each of the pixels in the first output for a reference die on the wafer from the characteristic of its corresponding pixel in the first output for a test die on the wafer;
   determining other values for pixels in second output for the wafer generated using a second optics mode of the inspection system, wherein determining the other values comprises determining a value of another characteristic of each of the pixels in the second output for the reference die and the other characteristic of its corresponding pixel in the second output for the test die, and wherein the first and second optics modes are different from each other;
   generating a two-dimensional scatter plot of the difference values and the other values for the pixels in the first and second output corresponding to substantially the same locations in the test die, wherein said generating is performed prior to outlier detection and defect detection for the wafer,
   generating an additional two-dimensional scatter plot for the first output, the second output, or the first and second output, wherein at least one value used to generate the additional two-dimensional scatter plot is different from the difference values and the other values used to generate the two-dimensional scatter plot;
   detecting defects in the test die on the wafer based on the two-dimensional scatter plot and the additional two-dimensional scatter plot; and
   binning the defects based on which of the two-dimensional scatter plot and the additional two-dimensional scatter plot in which the defects were detected, wherein said detecting comprises identifying outliers in the two-dimensional scatter plot and determining if the outliers correspond to defects, wherein generating the two-dimensional scatter plot is further performed prior to identifying the outliers in the two-dimensional scatter plot and determining if the outliers correspond to the defects, and wherein determining the difference values, determining the other values, generating the two-dimensional scatter plot, generating the additional two-dimensional scatter plot, detecting the defects, and binning the defects are performed by a computer system.

2. The method of claim 1, wherein the characteristic and the other characteristic are intensity of the pixels in the first output and the second output, respectively.

3. The method of claim 1, wherein the difference values are values for a linearly filtered difference, a match filtered difference, a non-linear filtered difference, a normalized difference, or a square root of a product of two differences.

4. The method of claim 1, wherein the other values are values for a median, a dilated median, or a range of median values.

5. The method of claim 1, wherein said detecting further comprises separating the two-dimensional scatter plot into two or more segments and separately performing defect detection in each of the two or more segments.

6. The method of claim 5, wherein one or more first defect detection parameters used for the defect detection in a first of the two or more segments are different than one or more second defect detection parameters used for the defect detection in a second of the two or more segments.

7. The method of claim 6, wherein the one or more first and second defect detection parameters comprise different thresholds that are applied to the difference values for the pixels in the first output for the test die.

8. The method of claim 1, wherein generating the additional two-dimensional scatter plot comprises determining other values for the pixels in the first output and generating the additional two-dimensional scatter plot of the difference values and the other values for the pixels in the first output.

9. The method of claim 8, further comprising displaying to a user the two-dimensional scatter plot and the additional two-dimensional scatter plot.

10. The method of claim 1, further comprising displaying to a user the two-dimensional scatter plot and allowing the user to change the difference values and the other values in the two-dimensional scatter plot by selecting the first and second optics modes from multiple optics modes of the inspection system used to generate output for the wafer, selecting the difference values from among different types of difference values that can be determined by the method, and selecting the other values from among different types of other values that can be determined by the method.

11. The method of claim 1, wherein the first and second output are generated in the same pass of an inspection process performed on the wafer by the inspection system.

12. The method of claim 1, wherein the first and second output are generated in different passes of a single inspection process performed on the wafer by the inspection system.

13. The method of claim 1, wherein the first and second output are generated in different passes of different inspection processes performed on the wafer by the inspection system.

14. A non-transitory computer-readable medium, storing program instructions executable on a computer system for performing a method for detecting defects on a wafer, wherein the method comprises:
    determining difference values for pixels in first output for a wafer generated using a first optics mode of an inspection system, wherein said determining comprises subtracting a characteristic of each of the pixels in the first output for a reference die on the wafer from the characteristic of its corresponding pixel in the first output for a test die on the wafer;
    determining other values for pixels in second output for the wafer generated using a second optics mode of the inspection system, wherein determining the other values comprises determining a value of another characteristic of each of the pixels in the second output for the reference die and the other characteristic of its corresponding pixel in the second output for the test die, and wherein the first and second optics modes are different from each other;
    generating a two-dimensional scatter plot of the difference values and the other values for the pixels in the first and second output corresponding to substantially the same locations in the test die, wherein said generating is performed prior to outlier detection and defect detection for the wafer;
    generating an additional two-dimensional scatter plot for the first output, the second output, or the first and second output, wherein at least one value used to generate the additional two-dimensional scatter plot is different from the difference values and the other values used to generate the two-dimensional scatter plot;
    detecting defects in the test die on the wafer based on the two-dimensional scatter plot and the additional two-dimensional scatter plot; and
    binning the defects based on which of the two-dimensional scatter plot and the additional two-dimensional scatter plot in which the defects were detected, wherein said detecting comprises identifying outliers in the two-dimensional scatter plot and determining if the outliers correspond to defects, and wherein generating the two-dimensional scatter plot is further performed prior to identifying the outliers in the two-dimensional scatter plot and determining if the outliers correspond to the defects.

15. A system configured to detect defects on a wafer, comprising:
    an inspection subsystem configured to direct light to a wafer and detect light from the wafer to thereby generate first output for the wafer with a first optics mode and second output for the wafer with a second optics mode, wherein the first and second optics modes are different from each other; and
    a computer subsystem configured for:
        determining difference values for pixels in the first output, wherein said determining comprises subtracting a characteristic of each of the pixels in the first output for a reference die on the wafer from the characteristic of its corresponding pixel in the first output for a test die on the wafer;
        determining other values for pixels in the second output, wherein determining the other values comprises determining a value of another characteristic of each of the pixels in the second output for the reference die and the other characteristic of its corresponding pixel in the second output for the test die;
        generating a two-dimensional scatter plot of the difference values and the other values for the pixels in the first and second output corresponding to substantially the same locations in the test die, wherein said generating is performed prior to outlier detection and defect detection for the wafer;
        generating an additional two-dimensional scatter plot for the first output, the second output, or the first and second output, wherein at least one value used to generate the additional two-dimensional scatter plot is different from the difference values and the other values used to generate the two-dimensional scatter plot;
        detecting defects in the test die on the wafer based on the two-dimensional scatter plot and the additional two-dimensional scatter plot; and
        binning the defects based on which of the two-dimensional scatter plot and the additional two-dimensional scatter plot in which the defects were detected, wherein said detecting comprises identifying outliers in the two-dimensional scatter plot and determining if the outliers correspond to defects, and wherein generating the two-dimensional scatter plot is further performed prior to identifying the outliers in the two-dimensional scatter plot and determining if the outliers correspond to the defects.

16. The system of claim 15, wherein the characteristic and the other characteristic are intensity of the pixels in the first output and the second output, respectively.

17. The system of claim 15, wherein the difference values are values for a linearly filtered difference, a match filtered difference, a non-linear filtered difference, a normalized difference, or a square root of a product of two differences.

18. The system of claim 15, wherein the other values are values for a median, a dilated median, or a range of median values.

19. The system of claim 15, wherein said detecting further comprises separating the two-dimensional scatter plot into two or more segments and separately performing defect detection in each of the two or more segments.

20. The system of claim 19, wherein one or more first defect detection parameters used for the defect detection in a first of the two or more segments are different than one or more second defect detection parameters used for the defect detection in a second of the two or more segments.

21. The system of claim 20, wherein the one or more first and second defect detection parameters comprise different thresholds that are applied to the difference values for the pixels in the first output for the test die.

22. The system of claim 15, wherein generating the additional two-dimensional scatter plot comprises determining other values for the pixels in the first output and generating the additional two-dimensional scatter plot of the difference values and the other values for the pixels in the first output.

23. The system of claim 22, wherein the computer subsystem is further configured for displaying to a user the two-dimensional scatter plot and the additional two-dimensional scatter plot.

24. The system of claim 15, wherein the computer subsystem is further configured for displaying to a user the two-dimensional scatter plot and allowing the user to change the difference values and the other values in the two-dimensional scatter plot by selecting the first and second optics modes from multiple optics modes of the inspection subsystem used to generate output for the wafer, selecting the difference values from among different types of difference values that can be determined by the computer subsystem, and selecting the other values from among different types of other values that can be determined by the computer subsystem.

25. The system of claim 15, wherein the first and second output are generated in the same pass of an inspection process performed on the wafer by the inspection subsystem.

26. The system of claim 15, wherein the first and second output are generated in different passes of a single inspection process performed on the wafer by the inspection subsystem.

27. The system of claim 15, wherein the first and second output are generated in different passes of different inspection processes performed on the wafer by the inspection subsystem.

* * * * *